Figure 1:
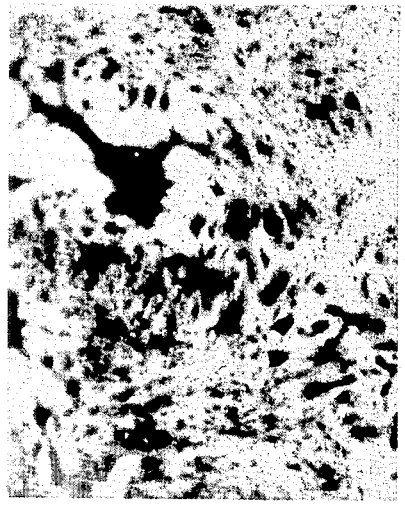
Figure 2:
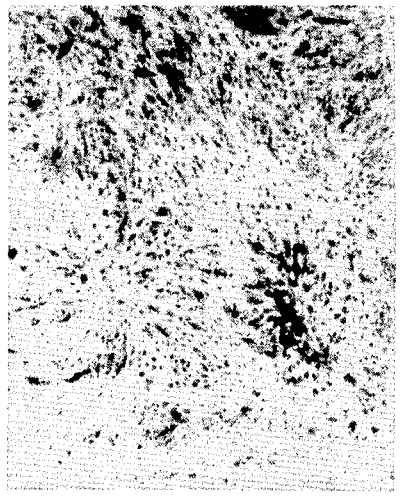
Figure 3:
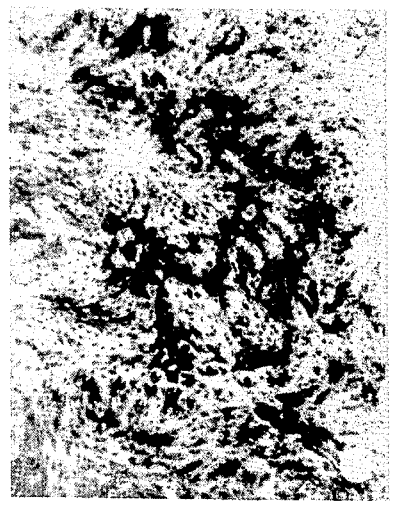
Figure 4:
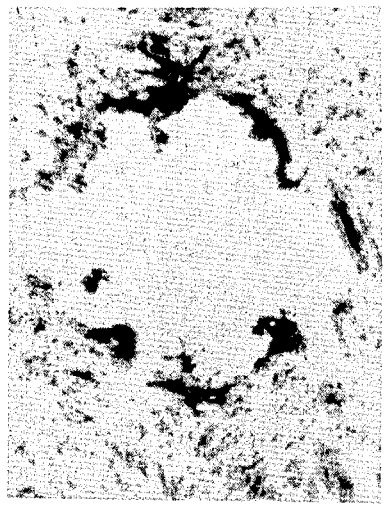

United States Patent [19]

Dubreuil, deceased et al.

[11] 4,211,843
[45] Jul. 8, 1980

[54] STRAIN OF MEASLES VIRUS AND PROCESS OF PRODUCING THE SAME

[75] Inventors: Robert Dubreuil, deceased, late of Montreal, Canada, by Monique Dubreuil, heir; Orvo Ast, Pierrefonds; Vytautas Pavilanis, Westmount, both of Canada

[73] Assignee: L'Institut Armand-Frappier, Laval, Canada

[21] Appl. No.: 856,202

[22] Filed: Nov. 30, 1977

[51] Int. Cl.² .................. A01N 1/02; A61K 39/12
[52] U.S. Cl. .................................... 435/2; 424/89
[58] Field of Search ................... 424/89; 195/1.8

[56] References Cited

U.S. PATENT DOCUMENTS

| | | | |
|---|---|---|---|
| 1,607,447 | 11/1926 | Degkwitz | 435/2 |
| 2,908,614 | 10/1959 | Muggleton et al. | 435/2 |
| 3,132,073 | 5/1964 | MacFarlane | 424/89 |
| 3,133,861 | 5/1964 | Schwarz | 424/89 |
| 3,214,340 | 10/1965 | Laurence | 435/2 |
| 3,468,758 | 9/1969 | Cabasso | 424/89 |

FOREIGN PATENT DOCUMENTS

| | | | |
|---|---|---|---|
| 960642 | 6/1964 | United Kingdom | 435/2 |
| 968980 | 9/1964 | United Kingdom | 435/2 |
| 1161414 | 8/1969 | United Kingdom | 435/2 |

OTHER PUBLICATIONS

G. Konovalov et al, Tsitologiya, 16, 10, 1268–1274, (1974) (English Translation), Isolation of Neurogrowth Factor and Detection of its Biological Activity.
R. Murphy et al., Proc. Nat'l. Acad. Sci. U.S.A., 74, No. 7, 2672–2676, (1977), Molecular Properties of NGF Secreted in Mouse Saliva.
M. Young et al, Biochem., 17, 8, 1490–1498, (1978), NGF: Multiple Dissociation Products in Homogenates of the Mouse Submandibular Gland.
S. Varon et al., Biochem., 6, 7, 2202–2209, (1967), Isolation of Mouse NGF Protein in a High Molecular Weight Form.
L. Greene et al, Biochem., 8, 9, 3735–3741, (1969), Subunit Interaction and Enzymatic Activity of Mouse 7S NGF.
A. Smith et al, Biochem., 8, 12, 4918–4925, (1969), Subunit Equilibria of 7S NGF Protein.
M. Baker, J. Biol. Chem., 250, 5, 1714–1717, (1975), Molecular Weight and Structure of 7S NGF Protein.
R. Murphy et al., Proc. Nat'l. Acad. Sci., (U.S.A.), 74, 6, 2330–2333, (1977), NGF in Mouse Serum and Saliva: Role of the Submandibular Gland.
N. Pantazis et al., Biochem., 16, 1525 (1977), Dissociation of 7S NGF Complex in Solution.
M. Young et al., Science, 187, 361–362, (1975), Secretion of NGF by Primary Fibroblast Cultures.
N. Pantazis et al, Proc. Nat'l. Acad. Sci., 74, 4, 1492–1496, (1977), Molecular Properties of NGF Secreted by L Cells.
R. Murphy et al., Proc. Nat'l. Acad. Sci. U.S.A., 72, 5, 1895–1898, (1975), Secretion of NGF by Mouse Neuroblastoma Cells in Culture.
J. Oger et al., Proc. Nat'l. Acad. Sci. U.S.A, 71, 4, 1554–1558, (1974), Synthesis of NGF by L and 3T3 Cells in Culture.

*Primary Examiner*—Frederick E. Waddell
*Attorney, Agent, or Firm*—Swabey, Mitchell, Houle, Marcoux & Sher

[57] ABSTRACT

The disclosure describes a process for the production of an attenuated strain of measles virus effective for the production of an attenuated measles virus vaccine. The starting material is an Edmonston strain of measles virus which has undergone a plurality of culture passages in various culture media. A sample of the last culture passage is taken and a plurality of culture passages of the sample is effected in primary cultures of fibroblasts of chicken embryos. A sample from the last culture passage is inoculated and a culture passage is effected in a primary culture of fibroblasts of chicken embryos thereby obtaining clones of virus. Clones of measles virus obtained in the last culture passage are isolated and one selects those which are thermosensitive at a temperature between about 32° C. and 37° C. Among the thermosensitive clones which have been selected, another selection is made of the ones with moderate cytopathic effect, and finally one isolates from the latest selection, the one which shows highest seroconversion on monkeys, thus producing an attenuated strain of measles virus.

9 Claims, 4 Drawing Figures

STRAIN OF MEASLES VIRUS AND PROCESS OF PRODUCING THE SAME

This invention relates to a process for the production of an attenuated strain of measles virus and to the new strain of measles virus thus obtained. More particularly, the invention relates to an attenuated measles virus vaccine and to a process for the preparation thereof.

Measles is a disease caused by a virus which is suffered both by children and adults. This disease is well under control in the highly developed countries because of the possibilities of vaccinations or good medical care of the persons which have not been vaccinated and who might have caught the disease. However, in underdeveloped countries, this disease reaches nearly catastrophic levels and therefore it is highly desirable that any efforts be made to provide suitable relief either by vaccination or other kinds of treatments.

It is well known that an individual which has not been immunized can be protected against the attack of a disease of viral nature be being immunized with a vaccine containing a living virus of the same nature, which is immunologically related to the virulent virus but which is not itself pathogenic. Such a vaccine may contain an attenuated strain which is derived by various known treatments from the virulent virus. A vaccine is suitable for vaccination if the virulence of the virus that it contains is low. The term virulence signals the degree of damage a germ (microbe) is able to cause to the organism it has invaded, under normal circumstances.

Therefore, like any other disease of viral origin, measles can and should be treated by vaccination with an attenuated measles virus. It is well known that in some other diseases of infectious nature, a dead germ can perform the function of the vaccine. However, such is not the case with measles and it is known that a measles vaccine should contain a living measles virus which is of course attenuated. The idea is to come up with a vaccine which has as little undesired secondary effects as possible.

The prior art is loaded with examples of vaccines which are produced by first obtaining attenuated forms of measles virus and incorporatng the micro-organism in some kind of diluent for injection to a person.

For example, the measles virus in virulent form was previously cultured in tissue culture on various substrates and it was allowed to multiply in chick embryo tissue. One of the most popular forms of measles virus vaccine has been derived from the Edmonston strain which has been developed by Enders et al (Enders, Katz, Medearis "Recent Advances in Knowledge of Measle Virus" in Perspectives in Virology, New York, John Wiley, 1959; Katz, Milovanovic and Enders, Proceedings of the Society for Experimental Biology and Medicine, vol. 97, pp. 23-29, 1958). The Edmonston strain was produced by Enders as a result of successive series of passages through human kidney tissue culture, human amnion tissue culture, embryonated eggs and chick embryo tissue culture. According to these methods of culture the virus was incubated in the culture medium, after incubation at temperatures between 35° C. and 37° C. The resulting cultured virus is attenuated to some extent which means that it is partially modified. However, it has been found out that inoculation of nonimmune humans produces relatively severe undesirable side effects, such as high fevers and the like. Also, children which have been immunized with the vaccine based on the Edmonston strain of measles virus often suffered from rash which is of course not acceptable. It will therefore be seen that the Edmonston strain was not completely acceptable because of the side effects especially in children. It was found that immunization with the Edmonston strain had to be accompanied by an injection of gamma globulin to protect the child from severe symptoms. This is of course not practical and it is quite expensive.

Schwartz in U.S. Pat. No. 3,133,861 describes a process for producing an attenuated measles virus vaccine which allegedly produces little or no undesirable reaction in children which are inoculated with the vaccine. The method broadly consists in culturing a live measles virus in avian embryo tissues at a temperature of about 28° C. to about 32° C. using a repeated number of culture passages until the attenuated virus produces in humans no or little undesirable reaction to the vaccine. The number of passages could be quite large, for example at least about 40 and therefore the process is quite complex, let alone time consuming.

We have found that it is possible to produce an attenuated strain of measles virus which is effective for the production of measles virus vaccine and which is free or substantially free of side effects, by a method which comprises:

selecting an Edmonston strain of measles virus which has undergone a plurality of culture passages in various culture media and taking a sample of the last culture passage;

effecting a plurality of culture passages of the sample obtained, in primary cultures of fibroblasts of chicken embryos;

selecting a sample from the last culture passage and effecting at least one culture passage thereof in a primary culture of fibroblasts of chicken embryos;

isolating clones of measles virus obtained in the last culture passage and selecting those which are thermosensitive at a temperature between about 32° C. and 37° C.;

among the thermosensitive clones which have been selected, making another selection of the ones with moderate cytophathic effect; and in final instance, isolating from the latest selection, the one which shows highest seroconversion on monkeys, thus producing an attenuated strain of measles virus.

Although the number of passages which the measles virus has to undergo through the various culture medium can vary to a large extent, the idea is that, in final analysis, the strain must be sufficiently attenuated to prevent the formation of side effects in the person which is being immunized. The Edmonston strain which has been subjected to the following culture passages:

(a) Twenty-four (24) culture passages in human kidney cells;

(b) Twenty-eight (28) culture passages in human amniotic cells;

(c) Six (6) culture passages in the amniotic sac of embryonated eggs;

(d) Thirteen (13) culture passages in cells of chicken embryos; followed by (e) Eleven (11) culture passages in cells of chicken embryos was used by us for this purpose.

In accordance with the preferred embodiment of the invention, the virus sample is thereafter subjected to a first culture passage in a primary culture of fibroblasts of chicken embryos maintained at 33° C. followed by a second culture at 33° C. passage in a primary culture of fibroblasts of chicken embryos.

The clones of measles virus from the second culture passage in a primary culture of fibroblasts of chicken embryos are isolated by inoculating the strain in Petri dishes kept in an incubator in a 5% $CO_2$ enriched atmosphere during about two hours at about 32° C., after which the cultures are drained and washed away using phosphate buffer saline, and a culture medium is added and incubation is allowed to take place for four to six days at 32° C., after which the liquid medium is replaced by a methyl cellulose medium and the cultures are again incubated at 32° C. for a period of about 3 to 4 days, until plaques appear and different clones can be separated. This is a well known technique which, according to the invention, has been used for the first time in further attenuating this virus strain.

The separation of the clones and the selection of the one which is most suitable for producing measles vaccine can be carried out in a number of ways. However, we found that it would be preferable to select fourty-seven (47) samples of virus from the clones which have been separated, which are incubated on chicken embryo primary cultures for an incubation period for about fourteen (14) days, after which seven (7) are retained which are thermosensitive at a temperature between about 32° C. and 37° C. Each of the seven (7) samples selected is treated for the purpose of isolating clones by producing plaques by the technical method described above. Each plaque is again isolated in order to select three (3) clones with moderate cytopatic effect, and finally, one of the three clones selected, the one which has highest seroconversion on monkeys, is separated and is frozen at a temperature of −70° C.

In order to produce a vaccine which is stable for a certain period of time, various stabilizers could be added. However, it has been found out, according to the invention, that especially for the purpose of using a vaccine in tropical climate, it would be useful to use a stabilizer which consists of dextran, monosodium glutamate, d-sorbitol and normal serum albumin (human).

Preferably, the attenuated measles virus is suspended in the harvest medium containing the live virus and the final concentration of the ingredients of the stabilizer in the virus suspension are the following:

| | |
|---|---|
| 1. Dextran (NBC) MW 60 000 to 90 000 | 5.0% |
| 2. Sodium glutamate (mono), (Fisher N° S-302 | 1.0% |
| 3. d-Sorbitol (hydrate) (glucitol) (General Biochemicals N° 50180) | 1.0% |
| 4. Normal Serum Albumin (Human) (25% solution) (Hyland N° 060-016) | 0.5% |

Other formulas, equally efficient are as follows:

| | | |
|---|---|---|
| (2) | Dextran | 5.0% |
| | Monosodium glutamate | 1.0% |
| | d-Sorbitol | 0.5% |
| | Normal Serum Albumin in 25% solution | 1.0% |
| (3) | Dextran | 5.0% |
| | Monosodium glutamate | 1.0% |
| | d-Sorbitol | 1.0% |
| | Normal Serum Albumin in 25% solution | 1.0% |
| (4) | Dextran | 6.0% |
| | Monosodium glutamate | 1.0% |
| | d-Sorbitol | 1.0% |
| | Normal Serum Albumin in 25% solution | 0.5% |
| (5) | Dextran | 6.0% |
| | Monosodium glutamate | 1.0% |
| | d-Sorbitol | 0.5% |
| | Normal Serum Albumin in 25% solution | 1.0% |
| (6) | Dextran | 6.0% |
| | Monosodium glutamate | 1.0% |
| | d-Sorbitol | 1.0% |
| | Normal Serum Albumin in 25% solution | 1.0% |

-continued

We will now give, for illustration purposes only an example of production of the new attenuated strain.

Source of virus:

An Edmonston strain of measles virus was obtained from Doctor J. F. Enders by Lederle Laboratories of American Cyanamid Company, Pearl River, N.Y. after the measles virus has been subjected to the following culture passages:

1. Twenty-four (24) culture passages in human kidney cells;
2. Twenty-eight (28) culture passages in human amniotic cells;
3. Six (6) culture passages in the amniotic sac of embryonated eggs;
4. Thirteen (13) culture passages in chick embryo cells.

After receiving this strain, Lederle Laboratories has subjected the virus to eleven (11) culture passages on chick embryo cells. A sample of the eleventh passage, in the form of a lyophilized vaccine was used as the starting material.

The virus was cultured a first time on a primary culture of fibroblasts of chicken embryos maintained at 33° C. The virus which has been larvested was distributed into many flasks and was kept at −75° C. The source designated "S-37" which was used for the production of batches of virus vaccine has been obtained from this first passage by means of a second culture passage on a primary culture of fibroblasts of chicken embryos. The absence of adventitious virus in the cultures used for these two passages was controlled by subcultures on cultures of fibroblasts of chicken embryos, on kidney cells of Cercopithecitae, on kidney cells of Rhesus monkey and by the RIF and Cofal tests.

Appropriate dilutions of the source S-37 have been inoculated on primary cultures of fibroblasts of chicken embryos in Petri dishes kept in an incubator in a 5% $Co_2$ enriched atmosphere during about two hours at 32° C. The cultures are then drained and washed with phosphate buffer saline after which more culture medium is added and incubation is allowed to take place for four to six days at 32° C. The liquid medium is then replaced by adding methyl cellulose and the cultures are then allowed again to stand at 32° C. for a period of three to four days. The cellular layer is then colored with neutral red at a concentration of 1:30000. After a careful microscopic examination, fourty-seven (47) plaques containing clones of virus were isolated. The virus of each of these plaques is cultured into Petri dishes containing fibroblasts of chicken embryo in liquid medium: one of the dishes was incubated at 37° C. and the other one at 32° C. The reason for this is that it is intended to determine which of the particular virus which is isolated still grows at 32° C. but stops growing at 37° C. In other words, the strain which is intended to be obtained should have little or no cytopatic effect at 37° C. After fourteen days of incubation, tests were made to determine which of the virus is still growing at 32° C. but is not growing at 37° C. In other words, these tests are made in order to determine those which are thermosensitive between 32° C. and 37° C. The value of 32° C. has been selected as the most practical. Of course, one could select a slightly lower or higher values although it has been found out that 32° C. is the most easy temperature with which operate. It was found out that seven (7) clones of virus have substantially no cytopatic effect at 37° C., while for these same virus, this effect was still there in cultures maintained at 32° C.

The liquids which are at the surface of the cultures maintained at 32° C. of these seven (7) sources were used to produce plaques by the same technical procedure is described above. Five (5) plaques were re-isolated from each of these sources and were separately tested for their cytopatic effects in liquid medium at 32° C. and 37° C. Tests were thereafter made to determine which of the sources are most suitable to provide a new strain, i.e. those which have the best morphology of the plaques and have the least cytopatic effect. Three (3) sources were retained which are designated as IMH-1, IMH-2 and IMH-3. Various tests were made with these three (3) sources and the IMH-2 was retained as a source of vaccine since, on the one hand, it gives products of better quality and on the other hand, the serologic conversion on monkey after intracerebral inoculation is also higher.

In the photos which illustrate the invention:

FIG. 1 is a microscopic enlargement of plaques of the Edmonston strain of measles virus;

FIG. 2 is a microscopic enlargement of plaques of the Schwarz strain;

FIG. 3 is a microscopic enlargement of the IMH-2 strain; and

FIG. 4 is a microscopic enlargement of a strain called "L'OISEAU" of a measles virus isolated from a clinical case of measles.

From the photos, it will be seen that the strain IMH-2 seems the best suitable for reproducing a strain of attenuated measles virus.

The source IMH-2 was selected as a result of various tests as indicated above, the main one being the serologic conversion on monkeys. It was found out that with the IMH-2 there was 90% seroconversion while with the IMH-1 it was only 75% seroconversion. The strain selected was therefore the IMH-2 which was used to produce a measles virus vaccine.

Once a suitable attenuated strain of measles virus is obtained it was decided to add a stabilizer to the vaccine having in mind that it will be used in countries with tropical climate coupled with long distance transportation. The question of temperature is very important.

Under these circumstances, a good stabilizer should offer the best protection possible during freeze-drying, it should provide good storage of the vaccine at 4° C. (refrigerator temperature) as well as at −25° C.

Obviously, after freeze-drying, the vaccine should remain quite intact. In view of the fact that good protection should be afforded at −25° C. as well as at 4° C. for as long as possible, it was found that a good stabilizer should contain the following ingredients:

1. Dextran;
2. sodium monoglutamate;
3. d-sorbitol;
4. normal serum albumin (human)

As an example, the following formula was used.

| | |
|---|---|
| Virus, suspended in the harvest Medium 199 (Earle) | = 75% |
| concentrated stabilizer 9/4 | = 25% |

In the suspension obtained, the final concentration of the ingredients pertaining to the stabilizer are:

| | | |
|---|---|---|
| 1. | Dextran (NBC) MW 60 000 to 90 000 | 5.0% |
| 2. | Sodium glutamate (mono), (Fisher N° S-302) | 1.0% |
| 3. | d-Sorbitol (hydrate) (glucitol) (General Biochemicals N° 50180) | 1.0% |
| 4. | Normal Serum Albumin (Human) (25% solution) (Hyland N° 060-016) | 0.5% |

One vial of 20 human doses contains 2.7 ml of the freeze-dried suspension, representing about 0.2 g of solid matter. To reconstitute the vaccine, 10 ml of diluent has to be added, bringing the final volume up to about 10.2 ml, in which each 0.5 ml represents one human dose.

The dilution factor is 10.2:2.7=3.7778. Thus, in the reconstituted vaccine the proportions are:

| | |
|---|---|
| Dextran, 5:3.7778 | = 1.3235% |
| Monosodium glutamate, 1:3.7778 | = 0.2647% |
| d-Sorbitol, 1:3.7778 | = 0.2647% |
| Human serum albumin (25%), 0.5:3.7778 | = 0.13235% |

The specific weight of the virus suspension with the stabilizer incorporated being about 1.026, the weight correction per human dose of 0.5 ml is 0.5×1.026=0.513 g and each human dose of 0.5 ml contains:

| | | |
|---|---|---|
| 1. | Dextran, 1.3235%; (0/513 × 1.3235): 100 = $6.7896^{-3}$g | =6.7896mg |
| 2. | Monos.glutam., 0.2647%; (0.513 × 0.2647): 100 = $1.3579^{-3}$g | = 1.3579mg |
| 3. | d-Sorbitol, 0.2647% | = 1.3579mg |
| 4. | Hum.serum albumin (25%), 0.13235%; (0.513 × 0.13235): 100 = $0.6789^{-3}$g | = 0.6789mg |

Different tests were made to determine the value of the new vaccine.

In a first test, studies were made to determine the seroconversion and to find the presence of virus in the throat.

Four (4) children, aged 9 to 12 months, were treated. At that time, tthey had no antibodies capable of neutralizing the measles virus.

Daily clinical examination

Local reaction: little blotch and induration the 3th day after vaccination, in one case (R-02);

Rectal temperature: 39.6° C. on the 9th day, followed by a small rash on the 11th and the 12th day on one child (R-04).

Nothing else was observed on these children.

The neutralizing antibodies 100 $TCID_{50}$ in tubes of BSC-1 cells at 33° C. were

| before vaccination | after vaccination |
|---|---|
| R-01 < 1/4 | 1/28 |
| R-02 < 1/4 | 1/18 |
| R-03 < 1/4 | 1/76 |

| -continued | |
|---|---|
| before vaccination | after vaccination |
| R-04 < 1/4 | 1/58 |

Swabbing out of throat

The samples were each cultured in 4 tubes of kidney cultures of cercopithecus. They were observed during 13 days and no cytopathic effect was attributable to the measles virus. The floating liquids were collected 13 days after the first culture. They were cultured again 13 days later during which they were carefully observed on each day. Negative results.

Another test was made to study the seroconversion and to find out the possible transmission of the virus.

Nineteen (19) children aged between 15 months and 10 years and 8 months old were observed on a dayly basis during 46 days. None of these children had any antibodies capable of neutralizing the measles virus at the time of the vaccination.

Twelve (12) children were vaccinated while the 7 others have received a diluent and these children were used as witnesses to study the possible transmission of the virus.

The children were kept 3 in each room, i.e. 2 who have been vaccinated and one witness, during 15 days.

Daily clinical examination

| Local reaction: | None. | |
|---|---|---|
| Rectal temperature: | on those vaccinated: | |
| | no. 326-1 | −38.9° C. the 5th and 12th days |
| | no. 305 | −39.4° C. the 9th day 38.9° C. the 10th and 11th days |
| | on the witnesses: | |
| | no. 319 | −39.4° C. the 4th day with coryza |
| | no. 305 | −38.9° C. the 5th day with coryza |
| | no. 326-3 | −38.9° C. the 12th, 13th 26th, 27th and 33th days. |
| Eruption: | on those vaccinated: | |
| | no. 319 (9) | in the thorax region with the 8th and 9th days |
| | no. 319 (8) | in the thorax region the 7th 8th and 9th days |
| | on the witnesses: | |
| | no. 319 (10) | in the thorax region the 8th and 9th days. |

Antibodies preventing hemagglutination after the 8th week:

| Vaccinated | Witnesses |
|---|---|
| No. 17 1/23 | No. 19 negative |
| No. 18 1/47 | |
| No. 14 1/47 | No. 16 negative |
| No. 11 1/79 | No. 13 negative |
| No. 12 1/39 | |
| No. 8 1/20 | No. 10 negative |
| No. 9 1/47 | |
| No. 5 1/32 | No. 7 negative |
| No. 6 1/20 | |
| No. 1 1/112 | No. 3 negative |
| No. 2 1/56 | No. 4 negative |

We claim:

1. A process for the production of an attenuated strain of measles virus effective for the production of an attenuated measles virus vaccine, which comprises:
    selecting an Edmonston strain of measles virus which has undergone a plurality of culture passages in various culture media, and taking a sample of the last culture passage;
    effecting a plurality of culture passages of said sample in primary cultures of fibroblasts of chicken embryos;
    inoculating a sample from the last culture passage and effecting a culture passage thereof in a primary culture of fibroblasts of chicken embryos thereby obtaining clones of said virus;
    isolating clones of measles virus obtained in the preceding step, and selecting those which are thermosensitive at a temperature between about 32° C. and 37° C.;
    among the thermosensitive clones which have been selected, making another selection of the ones with moderate cytopathogenic effect; and
    finally isolating from the latest selection, the one which shows highest seroconversion on monkeys, thus producing an attenuated strain of measles virus.

2. A process according to claim 1, wherein said Edmonston strain has undergone twenty-four (24) culture passages in human kidney cells, twenty-eight (28) culture passages in human amniotic cells, six (6) culture passages in the amniotic sac of embryonated eggs and thirteen (13) culture passages in cells of chicken embryos, followed by eleven (11) culture passages in cells of chicken embryos.

3. A process according to claim 2, which comprises:
    effecting a first culture passage of said virus sample in a primary culture of fibroblasts of chicken embryos maintained at 33° C., followed by a second culture passage in a primary culture of fibroblasts of chicken embryos at 33° C.

4. A process according to claim 1, wherein clones of measles virus are isolated by inoculating the strain derived from the last culture passage in a primary culture of fibroblasts of chicken embryos, in petri dishes kept in an incubator in a 5% $CO_2$ enriched atmosphere during about 2 hours at about 32° C., after which the cultures are drained and washed with phosphate buffer saline and a culture medium is added and incubation is allowed to take place for four to six days at 32° C., after which the liquid medium is replaced by a methyl cellulose medium and the cultures are again incubated at 32° C. for a period of about 3 to 4 days, until plaques appear and different clones can be separated.

5. A process according to claim 4, wherein forty-seven (47) samples of virus are selected from the separated clones, and are incubated for an incubation period of about 14 days, after which seven are retained which are thermosensitive at a temperature between about 32° C. and 37° C., each of the seven samples selected is treated for the purpose of isolating clones by producing plaques, each plaque is again isolated in order to select three clones with moderate cytopathic effect, and finally, of the three clones selected, the one which has highest seroconversion on monkeys is separated and is frozen at a temperature of −75° C.

6. A process according to claim 5 which comprises suspending the attenuated measles virus in a harvest medium and adding a stabilizer comprising dextran, monosodium glutamate, d-sorbitol and normal serum albumin (human).

7. A process according to claim 6, wherein the amount of stabilizer in the composition is the following:

| | |
|---|---|
| - dextran: | 5.0% |
| - monosodium glutamate: | 1.0% |
| - d-sorbitol: | 1.0% |
| - normal serum albumin (human) (25% solution): | 0.5%. |

8. A measles vaccine whenever produced by the process of claim 1, 5 or 6.

9. A measles vaccine whenever produced by the process of claim 7 or 8.

* * * * *